United States Patent
Kwak et al.

(10) Patent No.: US 11,092,590 B2
(45) Date of Patent: Aug. 17, 2021

(54) STRIP MODULE AND METHOD FOR ACQUIRING INFORMATION OF A SAMPLE

(71) Applicant: Samsung Electronics Co., Ltd., Gyeonggi-do (KR)

(72) Inventors: Hyun-suk Kwak, Seoul (KR); Joo-won Rhee, Gyeonggi-do (KR); Chang-bae Lim, Gyeonggi-do (KR)

(73) Assignee: Samsung Electronics Co., Ltd

( * ) Notice: Subject to any disclaimer, the term of this patent is extended or adjusted under 35 U.S.C. 154(b) by 267 days.

(21) Appl. No.: 15/605,406

(22) Filed: May 25, 2017

(65) Prior Publication Data
US 2017/0343480 A1    Nov. 30, 2017

Related U.S. Application Data

(60) Provisional application No. 62/341,314, filed on May 25, 2016.

(30) Foreign Application Priority Data

Aug. 26, 2016  (KR) .................. 10-2016-0109444
Dec. 20, 2016  (KR) .................. 10-2016-0174253

(51) Int. Cl.
```
G01N 33/487    (2006.01)
G01N 21/84     (2006.01)
G01N 33/66     (2006.01)
G01N 21/77     (2006.01)
```
(52) U.S. Cl.
CPC ... *G01N 33/48785* (2013.01); *G01N 21/8483* (2013.01); *G01N 33/66* (2013.01); *G01N 2021/7759* (2013.01); *G01N 2201/062* (2013.01); *G01N 2201/12* (2013.01)

(58) Field of Classification Search
CPC .... G01N 21/78; G01N 33/66; G01N 21/8483; G01N 33/48785; G01N 21/251; G01N 2201/12; G01N 2021/7759; G01N 2201/062
See application file for complete search history.

(56) References Cited

U.S. PATENT DOCUMENTS

| | | |
|---|---|---|
| 8,935,007 B2 | 1/2015 | Kloepfer et al. |
| 9,057,702 B2 | 6/2015 | Ozcan et al. |
| 9,241,663 B2 | 1/2016 | Jena et al. |

(Continued)

FOREIGN PATENT DOCUMENTS

| KR | 100526556 | 11/2005 |
|---|---|---|
| KR | 1020140127766 | 11/2014 |

(Continued)

*Primary Examiner* — Dennis White
(74) *Attorney, Agent, or Firm* — The Farrell Law Firm, P.C.

(57) ABSTRACT

A method for measuring blood glucose levels by a portable terminal using a strip module is provided. The strip module includes a dye pad having a color that changes in response to a sample applied to the dye pad. The strip module also includes a transparent strip having a first side and a second side. The first side is opposite the second side. The dye pad is mounted on the first side of the transparent strip, and the transparent strip reflects light provided from a light source of a portable terminal located adjacent to the second side and transmits the light to the dye pad.

8 Claims, 30 Drawing Sheets

(56) References Cited

U.S. PATENT DOCUMENTS

| | | | |
|---|---|---|---|
| 2003/0044317 A1* | 3/2003 | Catt | B01L 3/5023 |
| | | | 422/402 |
| 2004/0191119 A1* | 9/2004 | Zanzucchi | A61B 5/14532 |
| | | | 422/504 |
| 2004/0219691 A1 | 11/2004 | Shartle et al. | |
| 2014/0170757 A1* | 6/2014 | Tsai | G01N 21/78 |
| | | | 436/55 |
| 2014/0170761 A1 | 6/2014 | Crawford et al. | |
| 2014/0273271 A1* | 9/2014 | Aizawa | G01N 33/558 |
| | | | 436/501 |
| 2015/0111228 A1 | 4/2015 | Kim et al. | |
| 2016/0080548 A1 | 3/2016 | Erickson et al. | |

FOREIGN PATENT DOCUMENTS

| | | |
|---|---|---|
| KR | 101507377 | 3/2015 |
| WO | WO 2013176458 | 11/2013 |

\* cited by examiner 130 140 150

(a)

(b)

(c)

STRIP MODULE AND METHOD FOR ACQUIRING INFORMATION OF A SAMPLE

PRIORITY

This application claims priority under 35 U.S.C. § 119(e) to U.S. Provisional Application No. 62/341,314, filed in the U.S. Patent & Trademark Office on May 25, 2016, and claims priority under 35 U.S.C. § 119(a) to Korean Patent Application No. 10-2016-0109444, filed in the Korean Intellectual Property Office on Aug. 26, 2016, and Korean Patent Application No. 10-2016-0174253, filed in the Korean Intellectual Property Office on Dec. 20, 2016, the contents of which are incorporated herein by reference.

BACKGROUND

1. Field of the Disclosure

The present disclosure relates generally to a strip module and a method for controlling a portable terminal, and more particularly, to a strip module for acquiring information of a sample using a light source and a camera of a portable terminal, and a method for controlling a portable terminal.

2. Description of the Related Art

Changes in living environments and eating habits have resulted in a rise in adult diseases such as hypertension and diabetes, and there is a greater concern regarding health conditions compared to the past. For example, patients who have a chronic disease, such as diabetes, are required to check their blood glucose levels by visiting a hospital, and also need to regularly check their blood glucose levels on their own to track their health conditions and take necessary actions. That is, diabetes patients may need to monitor blood glucose levels 6 times a day to control it at an appropriate level.

In order to acquire health information, such as a blood glucose level, as illustrated in FIG. 1A, a red LED 110 is lit on a pad 120, where a blood sample is injected for measurement by a sensor 130, to check a reflection intensity on the pad 120, which is changed by blood glucose. In order to measure a blood glucose level, a measuring device having a separate LED light is required. Additionally, a strip module for measuring blood glucose, as illustrated in FIG. 1B, has a punched hole 130 to photograph a pad 150 upon which a blood sample is provided, and a transparent film 140 to protect the pad 150 on the punched hole 130. The strip module has a complicated manufacturing process and an expensive manufacturing cost.

In order to measure blood glucose every day, diabetes patients need to bring a separate blood glucose measuring device, and use a disposable strip module, which is expensive, and thus, increases an economic burden on the patients.

SUMMARY

An aspect of the present disclosure provides a strip module for measuring information of a blood sample more conveniently and economically using a light source and a camera of a portable terminal, and provides a method for acquiring information on a sample by a portable terminal.

According to an embodiment of the present disclosure, a strip module is provided that includes a dye pad having a color that changes in response to a sample applied to the dye pad. The strip module also includes a transparent strip having a first side and a second side. The first side is opposite the second side. The dye pad is mounted on the first side of the transparent strip, and the transparent strip reflects light provided from a light source of a portable terminal located adjacent to the second side and transmits the light to the dye pad.

According to an embodiment of the present disclosure, a method is provided for controlling a portable terminal. A light source of the portable terminal is operated in response to a command to start measuring a blood glucose level. A dye pad is photographed into which a sample is inserted and which is disposed on a transparent strip coupled to the portable terminal. An image of the dye pad is analyzed and information regarding the sample is acquired. The information regarding the sample is output.

According to an embodiment of the present disclosure, a strip module is provided. The strip module includes a transparent strip having a first side and a second side. The first side is opposite the second side. The strip module also includes a dye pad disposed in a first area on the first side of the transparent strip and having a color that changes in response to a sample applied to the dye pad. The transparent strip internally reflects light provided at a second area of the second side to illuminate the dye pad. The first area is disposed laterally away from the second area along a length of the transparent strip.

BRIEF DESCRIPTION OF THE DRAWINGS

The above and/or other aspects, features, and advantages of the present disclosure will be more apparent from the following detailed description when taken in conjunction with the accompanying drawings, in which.

DETAILED DESCRIPTION

Figure 1A:
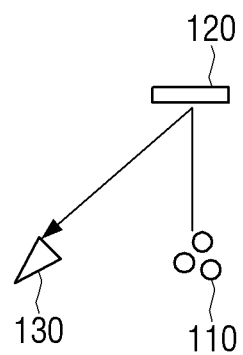
FIGS. 1A and 1B are diagrams illustrating a conventional method to measure information of a sample.
Figure 1B:
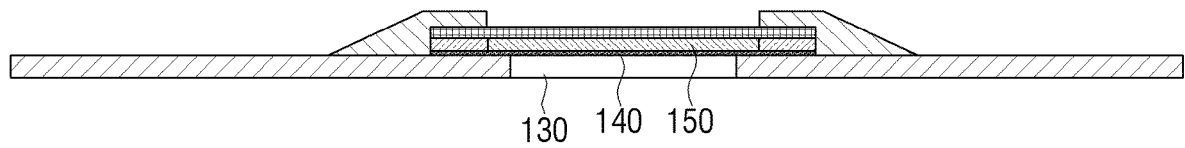

Embodiments of the present disclosure are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present disclosure.

Herein, relational terms, such as first and second, and the like, may be used to distinguish one entity from another, without necessarily implying any actual relationship or order between such entities.

The terms used herein are provided to describe specific embodiments and are not intended to limit the scope of an inventive concept. A singular term includes a plural form unless clearly defined otherwise. The terms "include" and "configured to", as used herein, indicate that there are features, numbers, steps, operations, elements, parts, or a combination thereof, and these terms should not exclude the possibility of a combination or an addition of one or more features, numbers, steps, operations, elements, parts, or a combination thereof.

As described herein, a module or a unit may perform at least one function or operation, and may be realized as hardware, software, or a combination thereof. In addition, a plurality of modules or units may be integrated into at least one module and may be realized as at least one process, except for modules or units that should be realized in specific hardware. When one element is referred to as being "connected to" another element, the elements may be directly connected or a third element may be connected in between. When an element is referred to as being "directly connected to" another element, the elements are directly connected without a third element connected in between.

Herein, the expression "configured to" can be used interchangeably with, for example, "suitable for", "having the capacity to", "designed to", "adapted to", "made to", or "capable of". The expression "configured to" does not necessarily mean "specifically designed to" in a hardware sense. Instead, under some circumstances, "a device configured to" may indicate that such a device can perform an operation along with another device or part. For example, the expression "a processor configured to perform A, B, and C" may indicate an exclusive processor (e.g., an embedded processor) to perform the corresponding operation, or a generic-purpose processor (e.g., a central processing unit (CPU) or application processor (AP)) that can perform the corresponding operations by executing one or more software programs stored in the memory device.

Technical terms used herein are to be used for the purpose of describing particular embodiments only, and are not intended to limit the present disclosure. In addition, the technical terms used herein are to be interpreted as is understood in the present specification by those of ordinary skill in the art, unless they are specifically defined by other means. Further, when technical terms do not accurately represent the features of the present disclosure, they may be replaced with meanings determined by one of ordinary skill in the art. In addition, the general terms used herein, which are defined as provided in advance, or which are to be interpreted according to the context before and after, are not to be construed as having a meaning in an excessively reduced manner.

Figure 2:
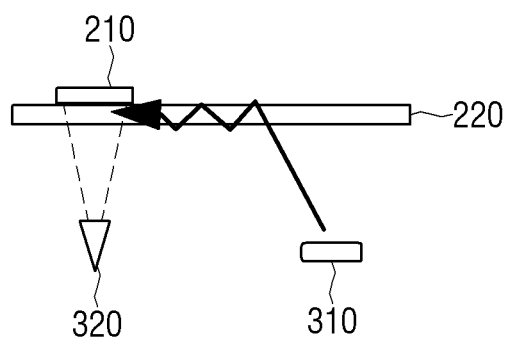
FIG. 2 is a diagram illustrating a strip module to acquire information of a sample, according to an embodiment of the present disclosure.

FIG. 2 is a diagram illustrating a strip module coupled to a portable terminal to obtain information of a sample, according to an embodiment of the present disclosure. As illustrated in FIG. 2, a strip module 200 includes a dye pad 210 and a transparent strip 220.

The dye pad 210 is positioned on the transparent strip 220 and may receive a sample for acquiring various information. A sample can be liquid, such as body fluid (for example blood, saliva, urine, sweat, etc.), but this is merely exemplary and the sample can also be gas or solid. In addition, the dye pad 210 can include a color change pad that responds to a specific material and changes color.

According to embodiment of the present disclosure, when the sample is blood, in order to determine whether there is disease and how much a disease progresses, the dye pad 210 may include color change pad to acquire information such as, for example, a blood glucose level, a cholesterol level, a cancer marker, a liver index, a lung index, a neutral fat level, a potassium level, a uric acid level, calcium receptor protein (Troponon) (CRP), N-terminal pro b-type natriuretic peptide (NT-proBNP), creatinine canase, and so on. Additionally, the dye pad 210 may include not only the color change pad for acquiring information on a disease, but also a color change pad for acquiring hormone information, such as, for example, a stress hormone level, a hair loss hormone level, a parathyroid hormone level, a female hormone level, a male hormone level, and a growth hormone level. In addition, the dye pad may include a color change pad for acquiring nutrition state information related to, for example, natrium, vitamin, and serum protein, and a color change pad for acquiring various health information related to, for example, ethanol, vitamin C, and folic acid.

According to an embodiment of the present disclosure, when a sample is sweat, the dye pad 210 can include a color change pad for acquiring health information related to, for example, lactic acid, acidity, and potassium.

When a sample is a tear or saliva, the dye pad 210 may include a color change pad for acquiring health information related to, for example, blood glucose or acidity.

When a sample is urine, the dye pad 210 can include a color change pad for acquiring various information related to, for example, blood glucose, ketone, acidity, blood, and white blood cell.

When a sample is water (e.g., drinking water, ground water, sewage, waste water, fish tank, and pool, etc.), the dye pad 210 may include a color change pad for acquiring information related to, for example, PH, hardness, inorganic substance, organic substance, bacteria, germs, etc.

When a sample is air, such as poison gas, the dye pad 210 may include a color change pad for acquiring information related to, for example, xylene, formaldehyde, ethylbenzene, toluene, acetone, cyclohexane, ethanol, methanol, etc.

When a sample is another air, solid, and solid substance included in air, the dye pad 210 may include a color change pad to for acquiring information related to, for example, micro dust, pollen, fungus, bacteria, virus, smog, nicotine, tobacco smoke, dandruff, and carbon dioxide.

When a sample is exhalation generated from an organism including human or animal, the dye pad 210 may include a color change pad for acquiring information regarding the substance of exhalation (e.g., NO, Pentane, Ethane, Aldehyde, CO, $CO_2$, Acetone($C_3H_6O$), Ketones, Alkanes, $H_2$, $O_2$, $N_2O$, $NH_3$, etc.)

When a sample is food, the dye pad 210 may include a color change pad for acquiring information regarding germs, virus, gas (for example, gas generated when kimchi ripens).

Referring back to FIG. 2, the dye pad 210 can be inkjet printed with colorimetric to measure blood glucose. The dye pad 210 may instead include a color change pad in a paper type, a coated color change pad, or superhydrophobic coated pad.

Dye in the dye pad 210 can be embodied as Methyl Orange, Chlorophenol red/Cresol red/Phenol red, BTB (Bromothymol Blue)/BPB (Bromophenol Blue), Bromocresol Green, m-cresol Purple, AAP+MADB, AAP+MAOS, Methylene Blue, Indigo Carmine, etc.

Figure 13:
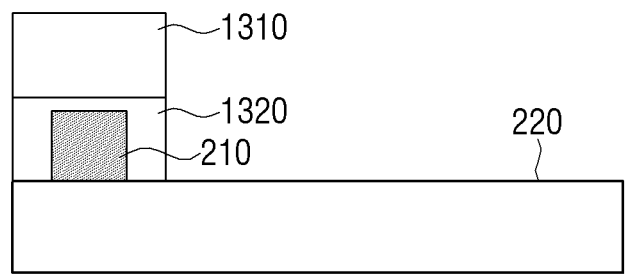
FIGS. 13 and 14 are diagrams illustrating a dye pad included in a strip module, according to embodiments of the present disclosure.

When a sample is air, in order to collect information regarding air more accurately, the dye pad 210 may further include a filter to remove vapor and a collection unit 1320 to increase concentration of a specific substance, as described in greater detail below with respect to FIG. 13.

Figure 14:
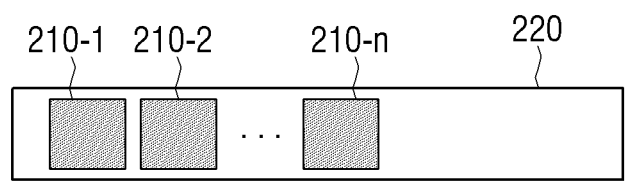

In FIG. 2, a single dye pad 210 is shown, but this is merely exemplary and in order to acquire various information at the same time, as illustrated in FIG. 14, a plurality of dye pads (210-1, 210-2, . . . 210-n) can be included. For example, when a sample is blood, the dye pad 210 may include a first dye pad 210-1 to measure a blood glucose level, a second dye pad 210-2 to measure a cholesterol level, and a third dye pad 210-3 to measure a liver index. As shown in FIG. 14, a plurality of dye pads are disposed in a length-wise direction, but this is merely exemplary and a plurality of dye pads can be disposed in a width-wise direction.

Through the various dye pads as described above, information relating to diseases, such as, for example, diabetes, heart disease, lung disease, liver disease, kidney disease, thyroid disease, inflammation, anemia, and cancer, as well as various health information, such as, for example, allergies, immune hormone, fatigue, alcohol, lack of water, nutritional status, lack of vitamin, glucose absorption disorder, etc. may be acquired. Through the various dye pads, an air pollution level, such as, for example, sick house syndrome, smoking, and fine dust can be acquired; water quality information, such as, for example, PH, hardness, inorganic substance, organic substance, bacteria, and virus can be acquired; food information, such as, for example, freshness, fermentation degree, ripening degree, and shelf life can be acquired; and disaster information relating to a fire can be acquired.

Figure 3:
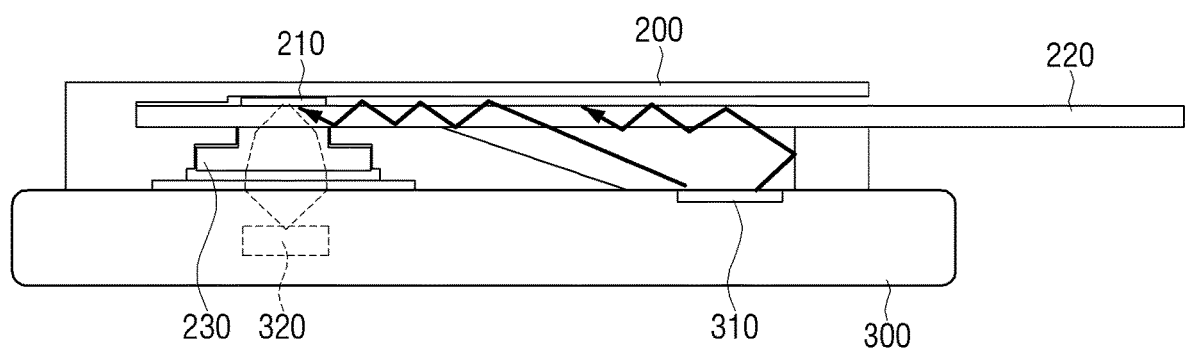
FIGS. 3, 4A, and 4B are diagrams illustrating a strip module coupled to a portable terminal to measure a blood glucose level, according to an embodiment of the present disclosure.

FIG. 3 is a diagram illustrating a strip module coupled with a mobile phone, according to an embodiment of the present disclosure. When the strip module 200 is coupled to a portable terminal 300, the dye pad 210 is positioned on a camera 320 of the portable terminal 300 and photographed by the camera 320 of the portable terminal 300.

The transparent strip 220 may reflect light generated from a light source 310 of the portable terminal 300, and transfer light to the dye pad 210 so that the camera 320 of the portable terminal 300 may photograph an area where the dye pad 210 is positioned.

In particular, the transparent strip 220 can be embodied as a transparent substance of which a refractive index is 1 or more, but this is merely exemplary, and even if the refractive index is less than 1, diffused light can be extracted, and light reflected through a translucent substance can be used.

In addition, the transparent strip 220 can be embodied as substance, such as, for example, polyethylene terephthalate (PET), polycarbonate (PC), poly vinil chloride (PVC), poly methyl methacrylate (PMMA), poly tetrafluoroethylene (PTEE), polystyrene (PS), hydrophilic polymers, polysaccharides (cellulose), polyacrylates, polyacrylamides, polyamines, polyglycols, hydrogels, hydrophobic polymers, flexible polymer, and acryl. In addition, the transparent strip 220 can be embodied in the shape of a square pillar, but this is merely exemplary, and the strip can be embodied as cylindrical pillar or polygonal pillar.

The transparent strip 220 can be composed of a transparent material without color, but this is merely exemplary, and can be a transparent substance with color (for example, red).

In order for the camera 320 of the portable terminal 300 to photograph the dye pad 210, the transparent strip 220 may conduct total reflection or diffused reflection of light provided from the light source 310 of the portable terminal 300 located at a specific surface (for example, a lower surface or an upper surface) of the transparent strip 220, and transmit the light to an area where the dye pad 210 is located. The camera 320 and the light source 310 can be disposed on the same surface with the transparent strip.

The camera 320 of the portable terminal 300 may photograph an area where the dye pad 210 is located by using light transmitted through the transparent strip 220. The light source 310 can be disposed below the transparent strip 220 and can be positioned in a right angle direction, a parallel direction, and a diagonal direction.

The light source 310 of the portable terminal 300 is a light emitting diode (LED), and a light generated from the light source 310 may be a white light or a daylight color light. However, this is merely exemplary, and the light source 310 of the mobile terminal 300 can be embodied as a fluorescent light or an incandescent light, and a light from the light source 310 can be a red light, a green light, or a blue light. In addition, light from the light source 310 can be in a visible ray area (400~700 mm), but this is merely exemplary, and can be ultraviolet rays (10~400 mm), infrared rays (700 nm~1 mm), near infrared (NIR) (0.75~1.4 μm), short wave infrared (SWIR) (1.4~3 μm), medium wave infrared (MWIR) (3~8 μm), long wave infrared (LWIR) (8~15 μm), far infrared (FIR) (15~1000 μm), etc. That is, the portable terminal 300 may photograph the dye pad 210 where a sample (for example, blood) is injected using the light source 310, which is generally for photographing an image. In addition, the portable terminal 300 may analyze the photographed image and measure information of a sample (for example, a blood glucose level).

A user may obtain information of various samples using the portable terminal 300, such as a smartphone, without a separate blood glucose measuring device.

An embodiment in which a sample is blood, and in which blood glucose information is acquired through the sample is described in detail below.

Figure 4A:
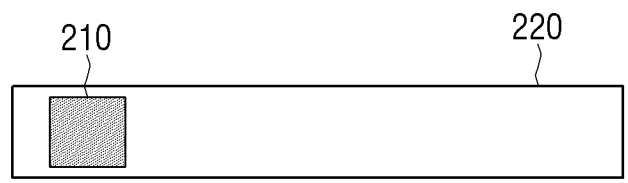
Figure 4B:
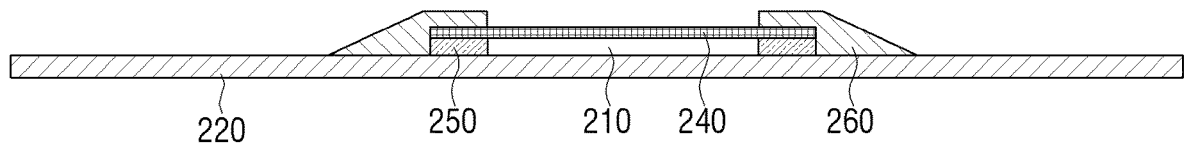

FIGS. 3, 4A, and 4B are diagrams illustrating a strip module coupled to a portable terminal operable to measure a blood glucose level, according to an embodiment of the present disclosure.

The strip module 200 may be coupled to the portable terminal 300 through a guide module or a housing. Specifically, the guide module is a case attachable to and detachable from the portable terminal 300 or a cover case of the portable terminal 300. The strip module 200 may be inserted into a guide module and coupled to the portable terminal 300. Alternatively, the strip module 200 may be coupled to the portable terminal 300 or a cover case of the portable terminal 300 through a coupling unit of the housing.

When the strip module 200 is coupled to the portable terminal 300, as illustrated in FIG. 3, a first area of the transparent strip 220 is positioned on the light source 310, and a second area of the transparent strip 220, where the dye pad of the transparent strip 220 is positioned, is positioned on the camera 320. That is, the light source 310 and the camera 320 are positioned in a straight line of a rear surface of the portable terminal 300, and the transparent strip 220 can be coupled to the portable terminal 300 to be parallel with the straight line in which the light source 310 and the camera 320 are positioned.

When a distance between the camera 320 and the dye pad 210 is a few mm, focusing can be difficult. Therefore, according to an embodiment of the present disclosure, a Fresnel lens 230 is positioned between the camera 320 and the dye pad 210. That is, the Fresnel lens 230 may further reduce focusing distance of the camera 320 so that a clearer image can be photographed. The Fresnel lens 230 may be provided on the housing of the strip module 200. The strip module 200 can adjust a focusing distance by using various focus adjustment devices, such as, for example, a convex lens and a concave lens in addition to the Fresnel lens 230.

As illustrated in FIG. 4A, the dye pad 210 is positioned on a specific area of the transparent strip 220. As illustrated in FIG. 4B, the dye pad 210, which is ink jet printed with colorimetric on the transparent strip 220, is formed. A mesh 240, which allows a blood sample pass through, is formed on the dye pad 210 using double-sided tape 250. The mesh 240 and the dye pad 210 are fixed to the transparent strip 220 by fixing tape 260.

The transparent strip 220, as illustrated in FIG. 3, can be embodied as transparent polymer material that may cause total reflection. For example, the transparent strip 220 may be embodied as transparent polymer having a refractive index that is greater than 1 (e.g., PET having a refractive index of 1.6 or PC and acryl having a refractive index of 1.58).

The transparent strip 220 may be embodied as semi-transparent material, which may transmit light, as well as transparent material. The transparent strip 220 may be embodied as a bar without a hole, as illustrated in (a) of FIG. 6F, a bar with a circular hole, as illustrated in (b) of FIG. 6F, or a bar with a rectangular hole, as illustrated in (c) of FIG. 6F. The hole is disposed in an area where the dye pad 210 is disposed so that totally reflected light can be radiated on blood sample as a ring light type to observe changes in light, and when color of the transparent strip 220 is red, the transparent strip 220 can function as a filter through which light source of a red wave area can pass. In particular, when measuring health information or disease information by injecting blood as a sample, a red filter role can be additionally required due to a phenomenon that a red blood cell included in blood leaks, and thus, more accurate measurement is available without an additional device through the transparent strip 220.

Accordingly, when a command to start measuring a blood glucose level is input to the portable terminal 300, the light source 310 of the portable terminal 300 may generate a white light, and the generated white light is totally reflected or diffusely reflected through the transparent strip 220, which transmits white light to an area where the dye pad is located. The camera 320 of the portable terminal 300 may photograph the dye pad into which a blood sample is injected using the reflected white light, and measure a blood glucose level by analyzing the photographed image.

The strip module 200 may further include a blood cell removal pad to remove blood cells of the blood sample. That is, for the portable terminal 300 to measure blood glucose more accurately, the blood cell removal pad may be disposed on the dye pad 210. Specifically, the electronic apparatus 300 analyzes a mode value in red color of blood to measure blood glucose. At this time, a red blood cell has red color and affects a mode value in red color of blood and it can obstruct measuring blood glucose. Therefore, more accurate measuring blood glucose can be possible by removing red blood cells through a blood cell removal pad.

Embodiments for coupling the strip module 200 with the portable terminal 300 or a cover case of the portable terminal 300 are described in greater detail below with reference to FIGS. 5A to 8.

Figure 5A:
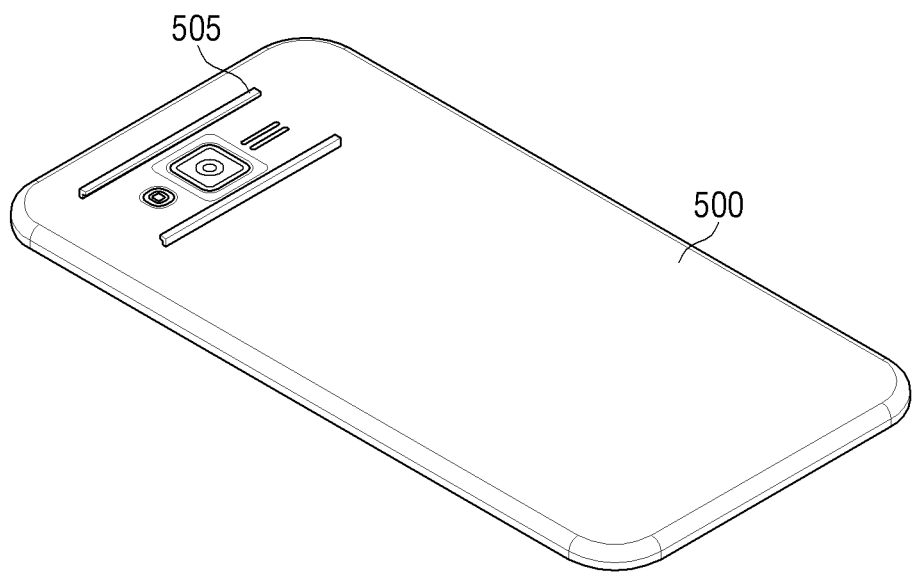
FIGS. 5A to 5C are diagrams illustrating the insertion of a strip module into a guide module coupled with a cover case, according to an embodiment of the present disclosure.
Figure 5B:
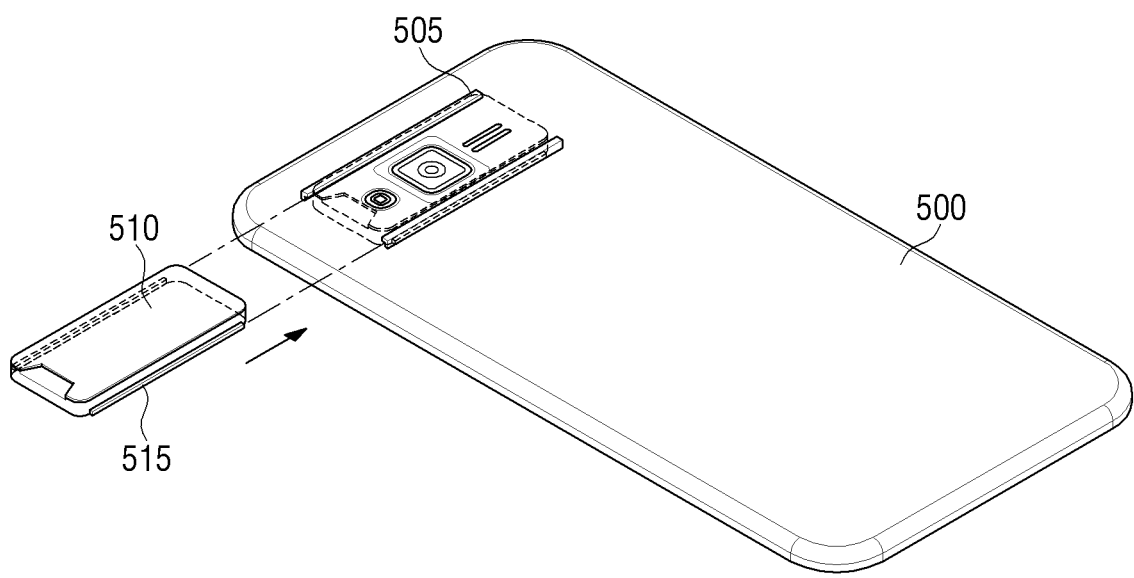
Figure 5C:
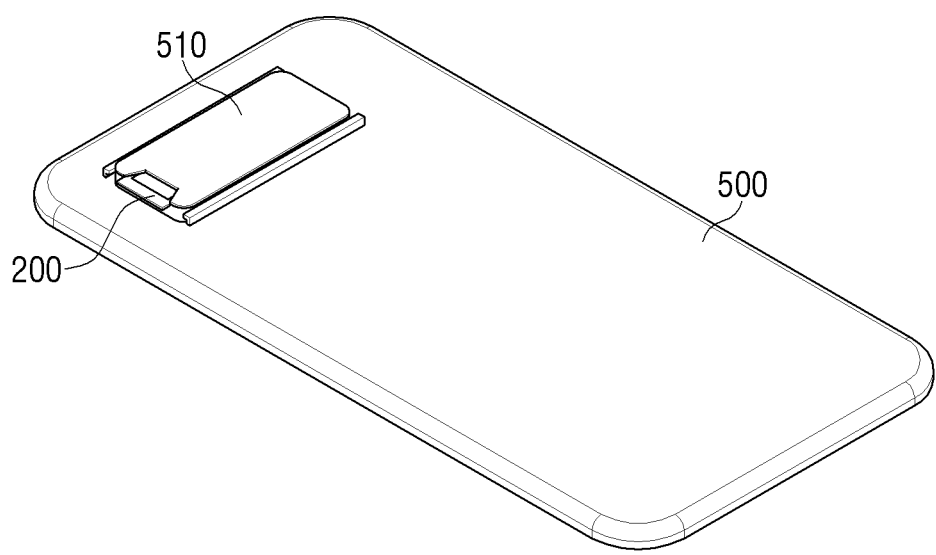

FIGS. 5A to 5C are diagrams illustrating the insertion of a strip module into a guide module coupled to a cover case, according to an embodiment of the present disclosure.

As illustrated in FIG. 5A, a cover case 500 includes a rail 505 to be coupled with a guide module 510. The cover case 500 is a case of an accessory type to protect a rear side of the portable terminal 300. However, coupling the guide module 510 with the cover case 500 is merely exemplary, and the guide module 510 can be directly coupled to a rear side where the light source 310 and the camera 320 are located. That is, the guide rail 505 to be coupled with the guide module 510 can be formed on a rear side of the portable terminal 300.

The guide module 510, as illustrated in FIG. 5B, includes the sliding guide 515, which slides along the guide rail 505, and the guide module 510 and the cover case 500 can be coupled.

Additionally, as illustrated in FIG. 5C, by inserting the strip module 200 into which a blood sample is inserted through a hole formed on the guide module 510, the strip module 200 can be coupled to the portable terminal 300.

That is, the camera 320 of the portable terminal 300 should be opened except in a case where the camera 320 measures blood glucose and when photographing a photo, the guide module 510 is detachable from the cover case 500. However, when measuring blood glucose levels, the guide module 510 can be attached to the cover case 500 and the dye pad 300 can be photographed using light generated from the light source 320. In addition, if the guide module 510 is stained with the blood sample, the guide module 510 can be detached for cleaning.

FIGS. 6A to 6E are diagrams illustrating a method for preparing a strip module including a housing, according to an embodiment of the present disclosure.

Figure 6A:
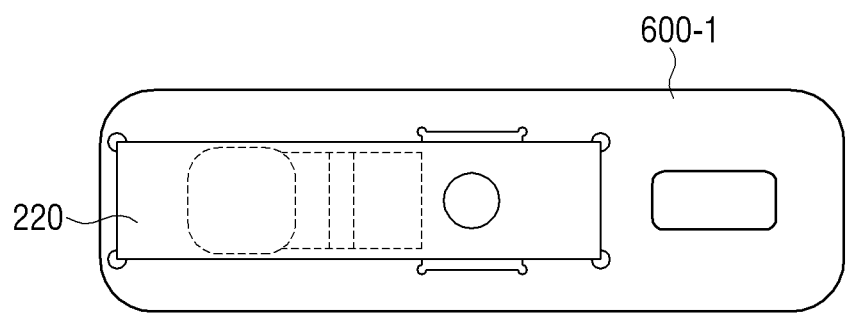
FIGS. 6A to 6F are diagrams illustrating a method for preparing a strip module including a housing, according to an embodiment of the present disclosure.

As illustrated in FIG. 6A, the transparent strip 220 is formed on a first housing 600-1. The first hole, which includes the camera 320 to photograph an area where the dye pad 210 is located, and the second hole, which includes light generated from the light source 310 to pass through, are formed in the first housing 600-1. In other words, the housing 600 of FIG. 6E, which includes the strip module 200, is coupled with the portable terminal 300, the first hole and the second hole may face the camera 320 and the light source 310. The first hole and the second hole can be round, but this is merely exemplary and they can be embodied as rectangular or polygonal. In addition, the first hole and the second hole may include a hinged structure and the first hole and the second hole can be opened only for sensing.

FIG. 6A illustrates that a hole is formed in an area where the dye pad 210 is formed from among the transparent strip 220, but this is merely exemplary, and for simple manufacturing, a hole may not be formed in an area where the dye pad 210 is formed from among the transparent strip 220.

Figure 6B:
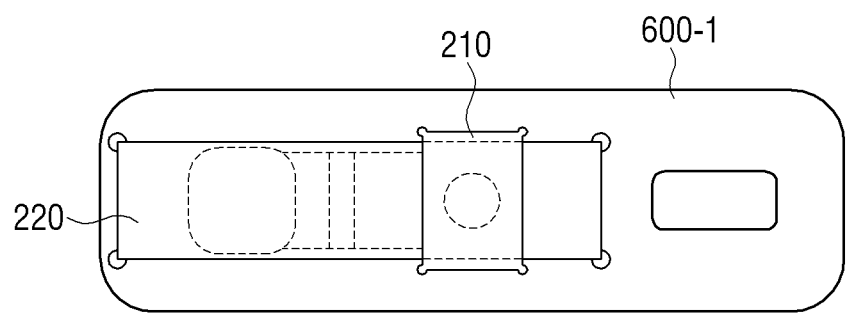
Figure 6C:
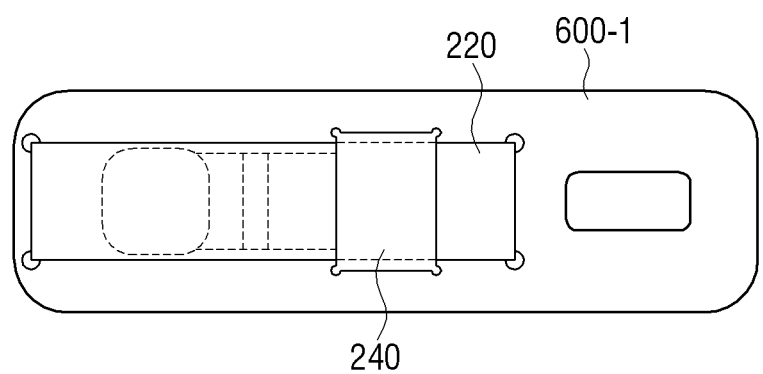

As illustrated in FIG. 6B, the dye pad 210 is formed on the transparent strip 220, and as illustrated in FIG. 6C, the mesh 240 may be formed on the dye pad 210. The mesh 240 may be fixed by the double-sided tape 250, and the dye pad 210 may be fixed by the fixing tape 260. In addition, the dye pad 210 and the mesh 240, as well as the blood cell removal pad, may be formed.

Figure 6D:
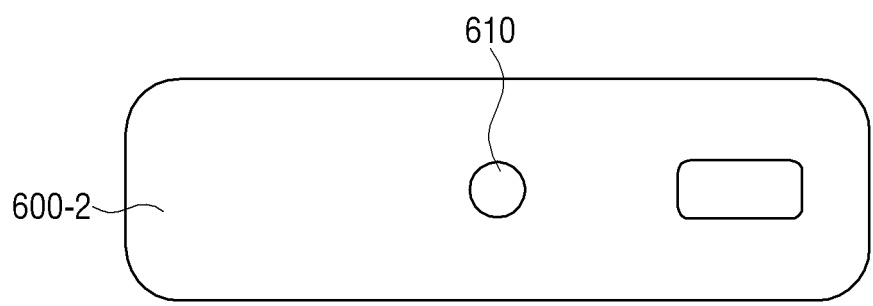

As illustrated in FIG. 6D, the transparent strip 220, which is coupled with a second housing 600-2 and the first housing 600-1, where the dye pad 210 is fixed can be housed. On the second housing 600-2, a hole 610 through which blood sample is injected may be formed.

Figure 6E:
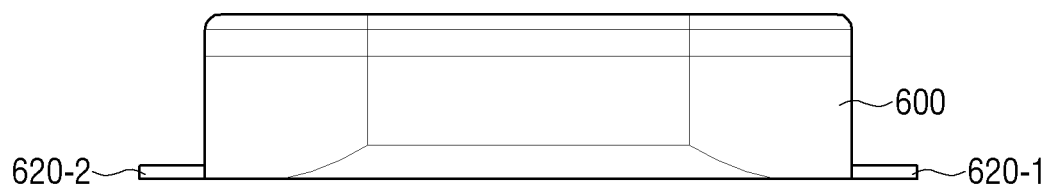
Figure 6F:
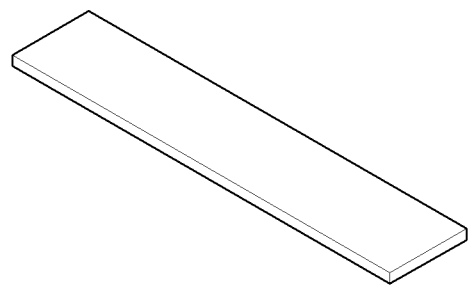
Figure 6F:
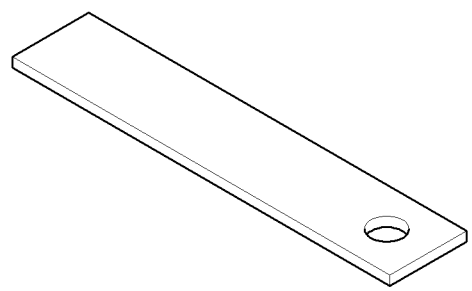
Figure 6F:
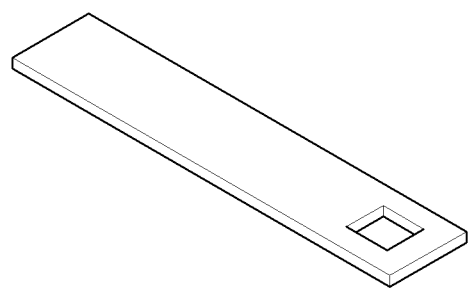

In a lower side area of the housing 600, where the first housing 600-1 and the second housing 600-2 are coupled, as illustrated in FIG. 6E, a sliding guide 620-1, 620-2, which is an example of a coupling unit operable to couple the housing with the portable terminal 300, can be formed. The housing 600 may be coupled with the portable terminal 300 through another configuration (for example, magnet, etc.)

Figure 7A:
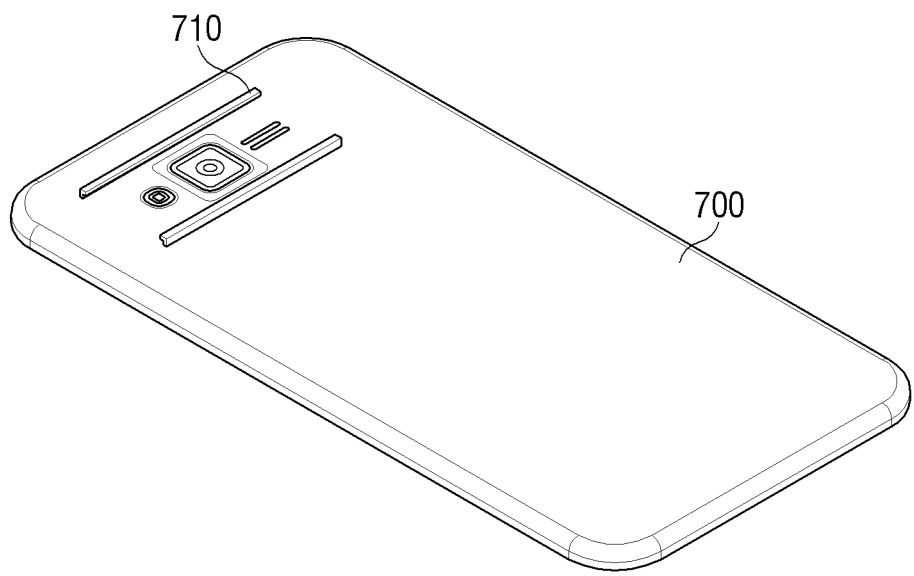
FIGS. 7A and 7B are diagrams illustrating the insertion of a strip module including a housing into a cover case of a portable terminal, according to an embodiment of the present disclosure.
Figure 7B:
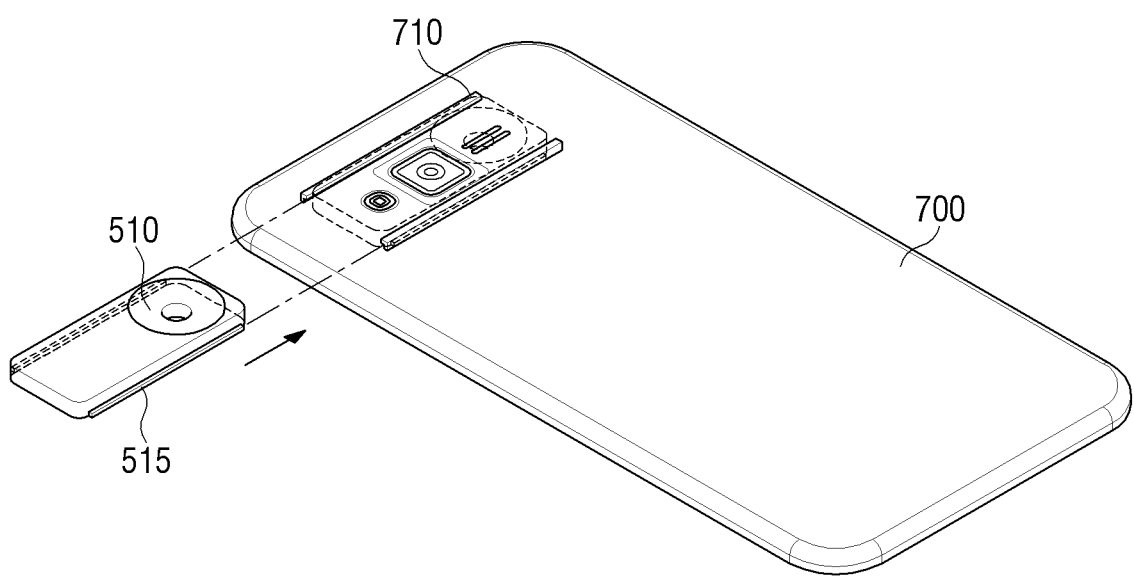

FIGS. 7A and 7B are diagrams illustrating the insertion of a strip module including a housing into a cover case of a portable terminal, according to an embodiment of the present disclosure.

As illustrated in FIG. 7A, a cover case 700 includes a guide rail 710 to be coupled with the housing 600. The cover case 700 is a case of an accessory shape to protect a rear side of the portable terminal 300. However, coupling the housing 600 with the cover case 700 is merely an exemplary embodiment, and the cover case 700 can be directly coupled with a rear side where the light source 310 and the camera 320 are located in the portable terminal 300.

The housing 600 including the transparent strip where the dye pad 210 is fixed, as illustrated in FIG. 6E, includes the sliding guide 620-1, 620-2, and the sliding guide 620-1, 620-2 slides along the guide rail 710.

As illustrated in FIGS. 5A to 5C, when the separate guide module 510 is coupled with the cover case 500 first and then the strip module 200 is inserted, and when the housing including the transparent strip 220 is coupled with the cover case 700, the camera 320 can be opened for photography, and when measuring blood glucose, the strip module 200 can be mounted.

Figure 8:
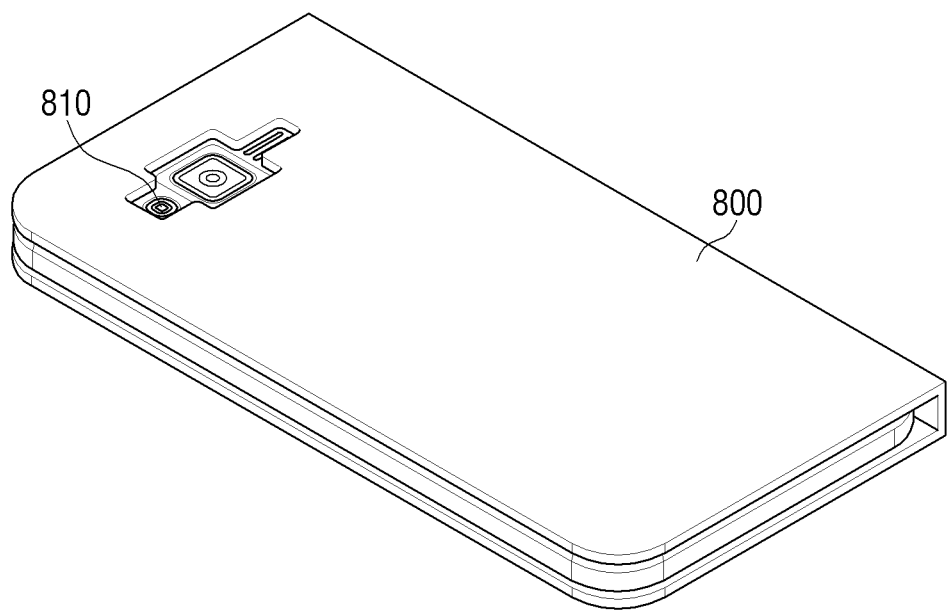
FIG. 8 is a diagram illustrating the insertion of a strip module including a housing into an accessory of a portable terminal, according to an embodiment of the present disclosure.
Figure 8:
Figure 8:
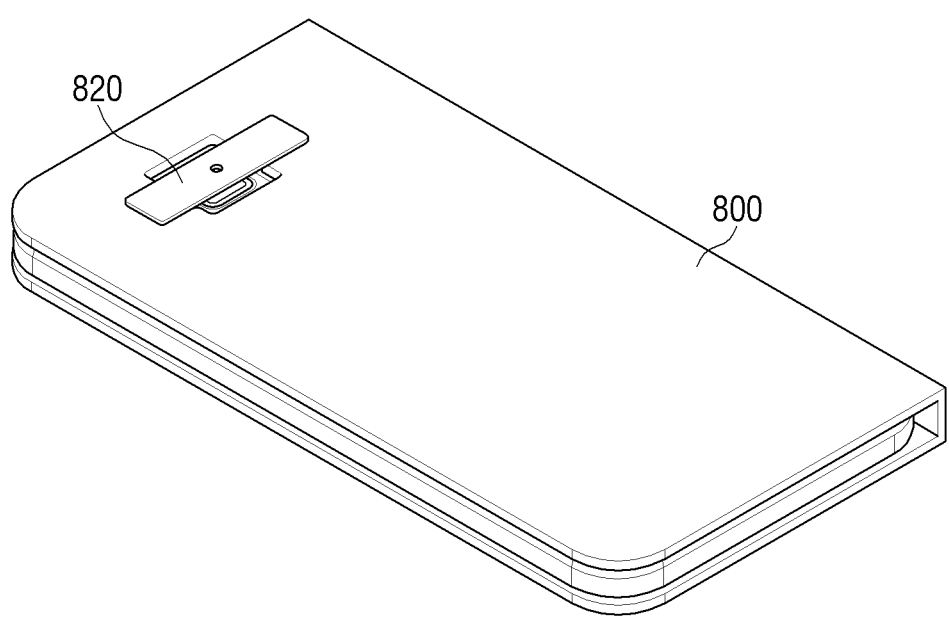

As illustrated in FIG. 8, a cover case 800 which entirely covers the portable terminal 300 may couple the a housing 820, which includes the transparent strip 220, to a hole 810 area that is formed to expose the light source 310 and the camera 320. The housing 820 may correspond to a shape and size of the hole area 810.

The portable terminal 300 for measuring a blood glucose level is described in greater detail below with reference to FIGS. 9-12.

Figure 9:
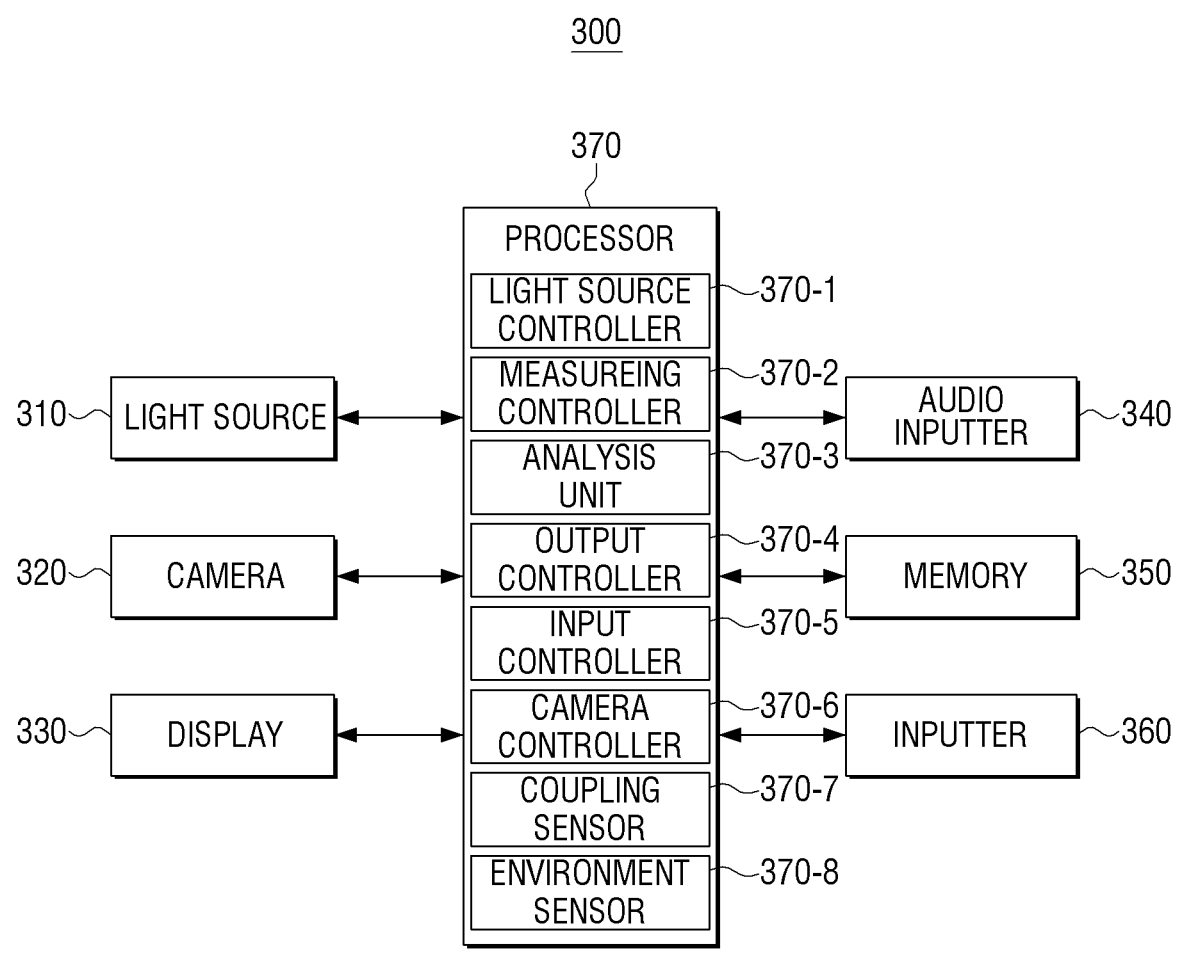
FIG. 9 is a block diagram illustrating a configuration of a portable terminal for measuring a blood glucose level, according to an embodiment of the present disclosure.

FIG. 9 is a block diagram illustrating the configuration of a portable terminal for measuring a blood glucose level, according to an embodiment of the present disclosure. As illustrated in FIG. 9, the portable terminal 300 includes the light source 310, the camera 320, the display 330, an audio outputter 340, a memory 350, an inputter 360, and a processor 370. The portable terminal 300 may be embodied as an electronic apparatus including the light source 310 and the camera 320, such as, for example, a mobile phone, smartphone, tablet personal computer (PC), notebook PC, smart watch, attachable patch, wearable device such as a necklace. In addition, the portable terminal 300 may be a home appliance such as a refrigerator, a washing machine, a kimchi refrigerator, an air conditioner, a cleaner, and an air washer, and an apparatus exclusive for measuring blood glucose.

The light source 310 may generate white light or daylight color light using LED. The light source 310 may be used as a flash for photographing a photo and as a role to generate light for measuring blood glucose.

The light source 310 may be provided on an area (for example, an upper area) of a rear side of the portable terminal 300, and disposed in a straight line with the camera 320. The light source 310 can be run or turned on or off by the control of the processor 370. An external screen fence can be provided outside the light source 310, and when a user uses the light source 310, the external screen fence can be removed.

The camera 320 photographs an image. The camera 320 may include a lens and an image sensor, and the image sensor may sense light transmitted through a lens and an image may be generated.

The camera 320 may have a short focal distance to enable photographing an image in a short distance as well as general photographing. For example, the camera 320 may photograph the dye pad 210 which is positioned several millimeters in front of the camera 320.

The display 330 displays various video data and a user interface (UI). In particular, the display 330 may provide an execution screen of an application and UI for measuring a blood glucose level.

The display 330 may be combined with a touch sensor and embodied as a touch screen, and as a flexible display type, may be coupled to at least one of a front area, a side area, and a rear area of the portable terminal 300. The flexible display can be bent, curved, or rolled without damage through thin and flexible substrate.

An audio outputter 340 is a configuration to output not only alarm sounds and voice messages, but also audio data for which various processing jobs, such as decoding, amplification, and noise filtering, are performed by the audio processor. The portable terminal 300 may further include an output terminal as a configuration to output audio. In particular, the audio outputter 340, when the display 330 of the portable terminal 300 is in a downward direction for measuring blood glucose, may output an audio guide to guide a method for measuring blood glucose.

The memory 350 stores various modules for driving the portable terminal 300. For example, the memory 350 may store software including a base module, a sensing module, a communication module, a presentation module, a web browser module, and a service module.

In addition, the memory 350 may store an application program for measuring blood glucose.

The inputter 360 may receive a user command for controlling the portable terminal 300. In addition, the inputter 360 may be embodied as a touch inputter, but this is merely exemplary and can be embodied as various input devices, such as a button inputter, a mouse, and a keyboard. Particularly, the inputter 360 may receive a user command to start measuring a blood glucose level.

A processor 370 may store overall operations of the portable terminal 300. In particular, when a command for starting measurement of a blood glucose level is input through the inputter 360, the processor 370 may operate or turn on the light source 310 of the portable terminal 300. In addition, the processor 370 may photograph a dye pad into which a blood sample is injected from among a transparent strip to which the portable terminal 300 is coupled, and measure blood glucose of a blood sample by analyzing a photographed image. That is, the processor 370 may control the display 330 or the audio outputter 340 to output information regarding the measured blood glucose.

When a command to start measuring blood glucose is input, the processor 370 may activate the camera 320. That is, the processor 370 may activate the camera 320 to obtain an image.

After the command to start measuring blood glucose is input through the inputter 360, when it is sensed that the transparent strip 220 is coupled with the portable terminal 300, the processor 370 may operate or turn on the light source of the portable terminal 300. The processor 370 may sense that the transparent strip 220 is coupled with the portable terminal 300 through various sensors.

When the light runs or turns on, the processor 370 may maintain an amount of light entering the image sensor of a camera by turning off an automatic exposure (AE) function.

The processor 370 may sense an external environment (e.g., external luminance, brightness, intensity of light, wave of light, change of temperature, color temperature, intensity of light, etc.) through various sensors, such as an illumination sensor, and a temperature sensor, and adjust brightness of the light source based on the sensed external environment. For example, the processor 370 may sense the light of the external environment, adjust the brightness of the light source 310 to be somewhat dark if the light of the external environment is brighter, and adjust the brightness of the light source 310 to be bright if the light of the external environment is darker. In addition, the processor 370 can control dimming, light color, color temperature, focusing, and color filter of the light source 310 according to a sensed external environment.

The processor 370 may photograph the dye pad 210, which is provided on an area of the transparent strip coupled with the portable terminal 300, and measure a blood glucose level of a blood sample injected into the dye pad 210. The processor 370 may analyze a red mode value included in a photographed image and measure the blood glucose level of the blood sample. That is, the processor 370 may measure a higher blood glucose level as the red mode value is lower, and may measure a lower blood glucose level as the red mode value is higher. In particular, the memory 350 may prestore a formula that converts blood glucose corresponding to the red mode value. A blood glucose level can also be measured using an average value and a median value, or a green mode value and a blue mode value can be used in addition to the red mode value.

The processor 370 may control the display 330 or the audio outputter 340 to provide information regarding the measured blood glucose value.

The processor 370, may output guide information regarding measuring blood through the audio outputter 340 while the display 330 of the portable terminal 300 is in a downward direction.

The processor 370 may store a measured blood glucose value and sense changes in the blood glucose value. When the blood glucose value exceeds a prestored normal scope, the processor 370 may output a warning message regarding blood glucose management or transmit health information to pre-registered contacts (for example, family, hospital, etc.). The processor 370 can transmit health information by using a telephone application, a message application, Internet application, etc.

The processor 370, by using a blood sample, may measure information relating to a lung disease, a blood disorder (for example, anemia), a thyroid disease, a heart disease, a metabolism disease, a liver disease (for example, hepatitis), an infection, an allergy, immune function, liver function, kidney function, cholesterol, etc. That is, the processor 370 may photograph the dye pad 210 to which blood sample is injected, analyze the color, and sense various health information.

The processor 370 may transmit a control signal to control an external device through a communicator (for example, WiFi, Bluetooth, Zigbee, infrared transmission, ultrasonic wave, cellular communication (3/4/5G), etc.) based on sensed health information. For example, when health information, such as heart disease cholesterol, diabetes, is obtained, the processor 370 may control the communicator to transmit cooking information, such as menu information, recipe information, and recommended food material, to a refrigerator. As another example, the processor 370 may transmit information regarding exercise time to a wearable device for exercise control. As still another example, the processor 370 may control the communicator to transmit a control signal to a window, a robot cleaner, an air-conditioner, and air cleaning device based on health information, such as allergic disease and lung disease. As still another example, the processor 370, when sensing a specific disease, may transmit health management information corresponding to disease information to smart drug box or smart cup. As still another example, the processor 370 may request fine dust information, etc. from an external device (for example, a sensor light provided on a front door) based on health information such as lung disease, flu, etc. As still another example, the processor 370 may request information regarding changes in body weight based on heath information such as thyroid disease and metabolism disease from an external device (for example, a sensor provided on a tile of a bathroom, a sensor provided on shoes, etc.). As still another example, the processor 370 can control the communicator to transmit a control command to an external device (for example, lighting device, air-conditioner, boiler, etc.) to adjust customized temperature and luminance for each disease.

The processor 370 may receive a signal requesting measurement of a blood glucose level from various external devices (such as refrigerator and smart cup before eating meal, bed after wake up, etc.). The processor 370, after exposure to an environment with a lot of cough and fine dust, may receive a signal requesting measurement of a value relating to the lungs from an external device.

In addition, the processor 370 may receive a request for exchanging a filter from an air washer, an air conditioner, and a cleaner, etc. The processor 370 can receive information, such as water intake information and water purifier cleaning state, from a water purifier and a smart cup, receive information on exposure to polluted air from a door, and acquire user information (for example, user movement information, meal amount information, etc.) from various sensors. The processor 370 may provide various health-related services with respect to information and sample received from the aforementioned external device.

The processor 370, as illustrated in FIG. 9, may include a light source controller 370-1 to control the light source 310, a measuring controller 370-2 to control operation of measuring the dye pad, an analysis unit 370-3 to analyze the sample of the photographed dye pad, an output controller 370-4 to control the display 330 and the audio outputter 340, an input controller 370-5 to control the inputter 360, a camera controller 370-6 to control the camera 320, a coupling sensor 370-7 to sense coupling with the strip module 200, and an environment sensor 370-8 to sense surrounding environment, such as intensity of illumination.

In addition, the portable terminal 300 may include various sensors, such as, for example, a chemical sensor, an electricity sensor, an ultrasonic sensor, and an optical sensor, and provide health information to a user by using information acquired by photographing the strip module 200 and information acquired through various sensors.

Measurement of a blood glucose level using the portable terminal 300 to which the strip module 200 is coupled is described in detail below with reference to FIGS. 10A to 10G. It is assumed the strip module 200 is housed by the housing 600.

Figure 10A:
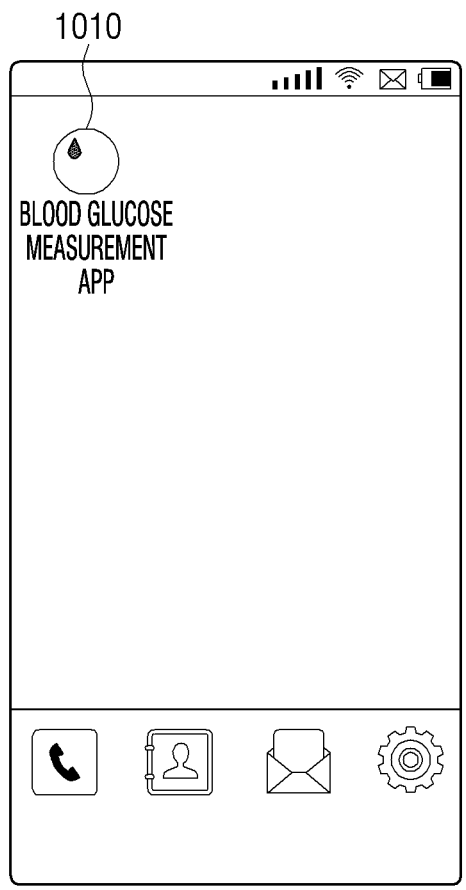
FIGS. 10A to 10G are diagrams illustrating measurement of a blood glucose level using a portable terminal where the strip module is coupled, according to an embodiment of the present disclosure.
Figure 10B:
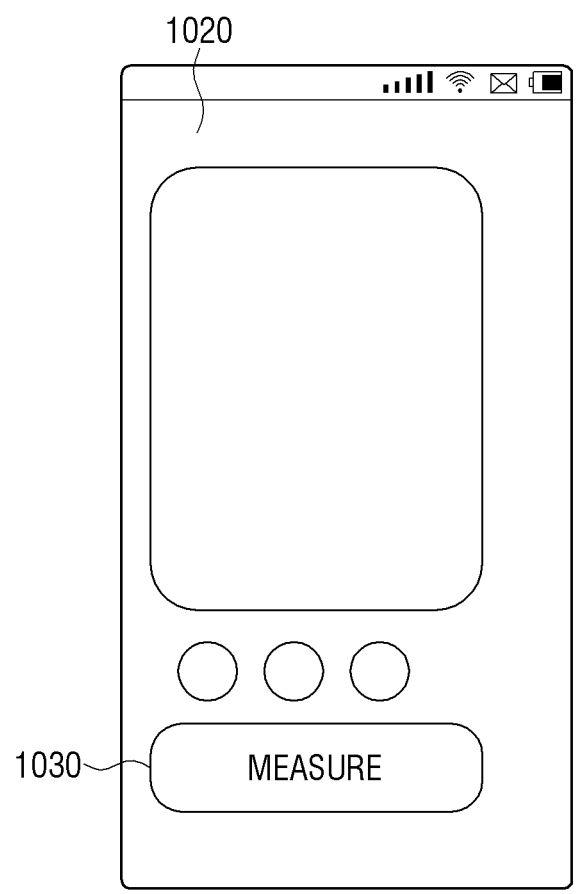
Figure 10C:
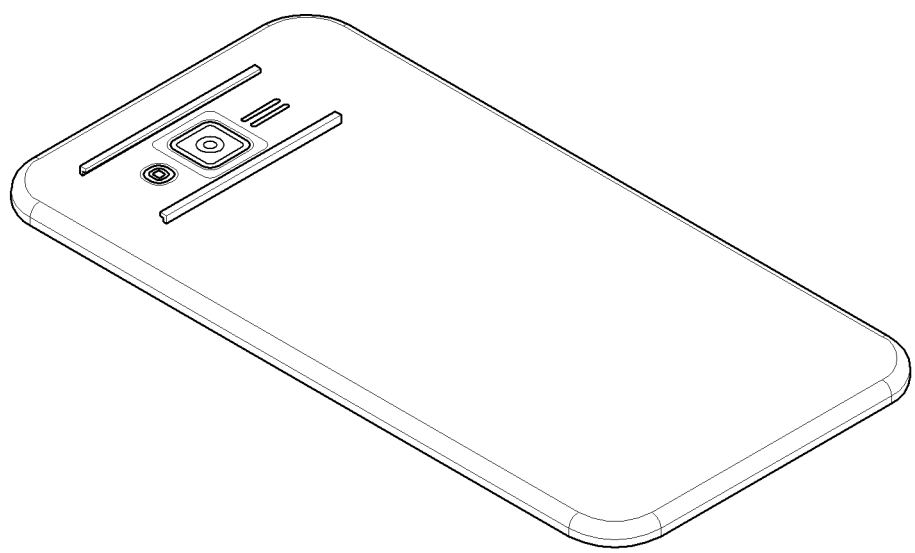
Figure 10D:
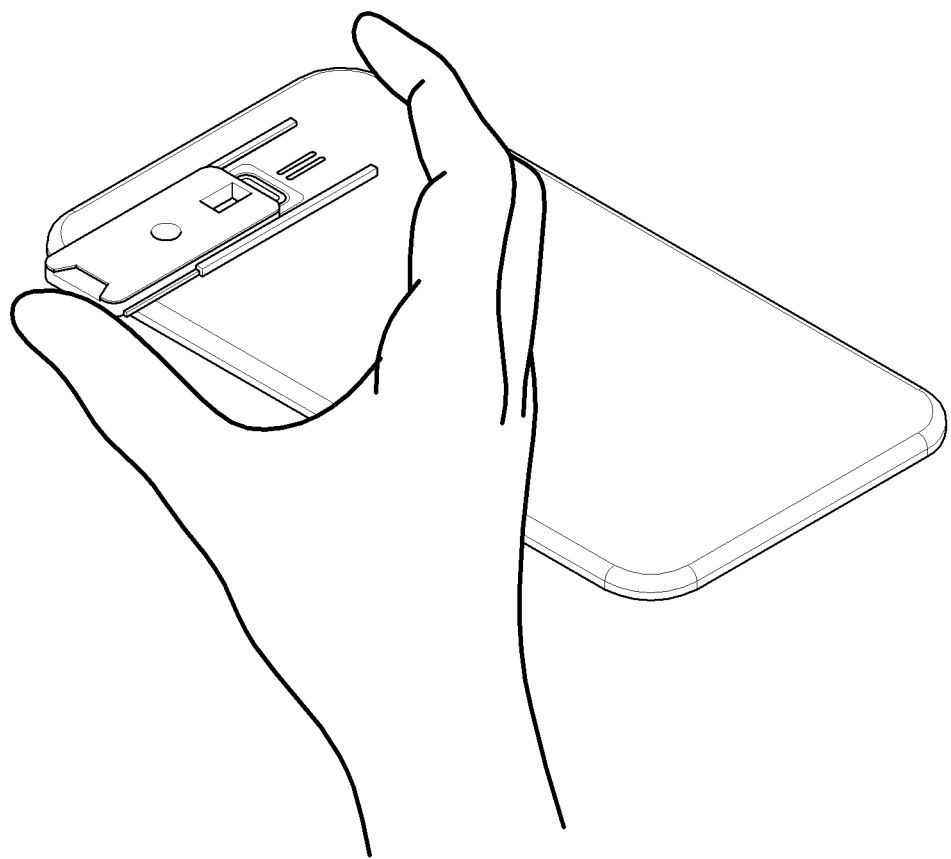
Figure 10E:
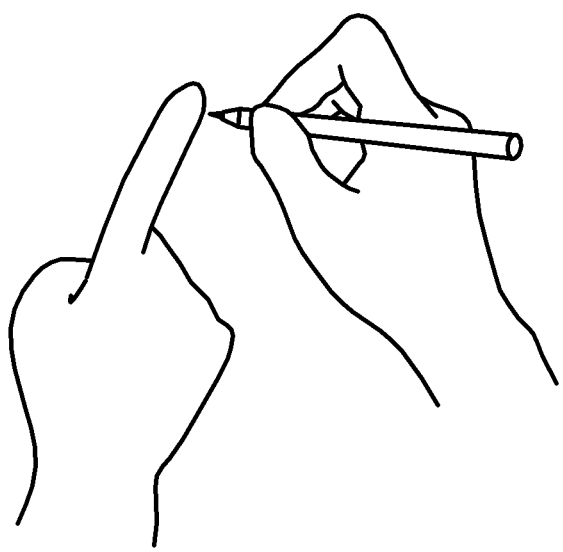
Figure 10F:
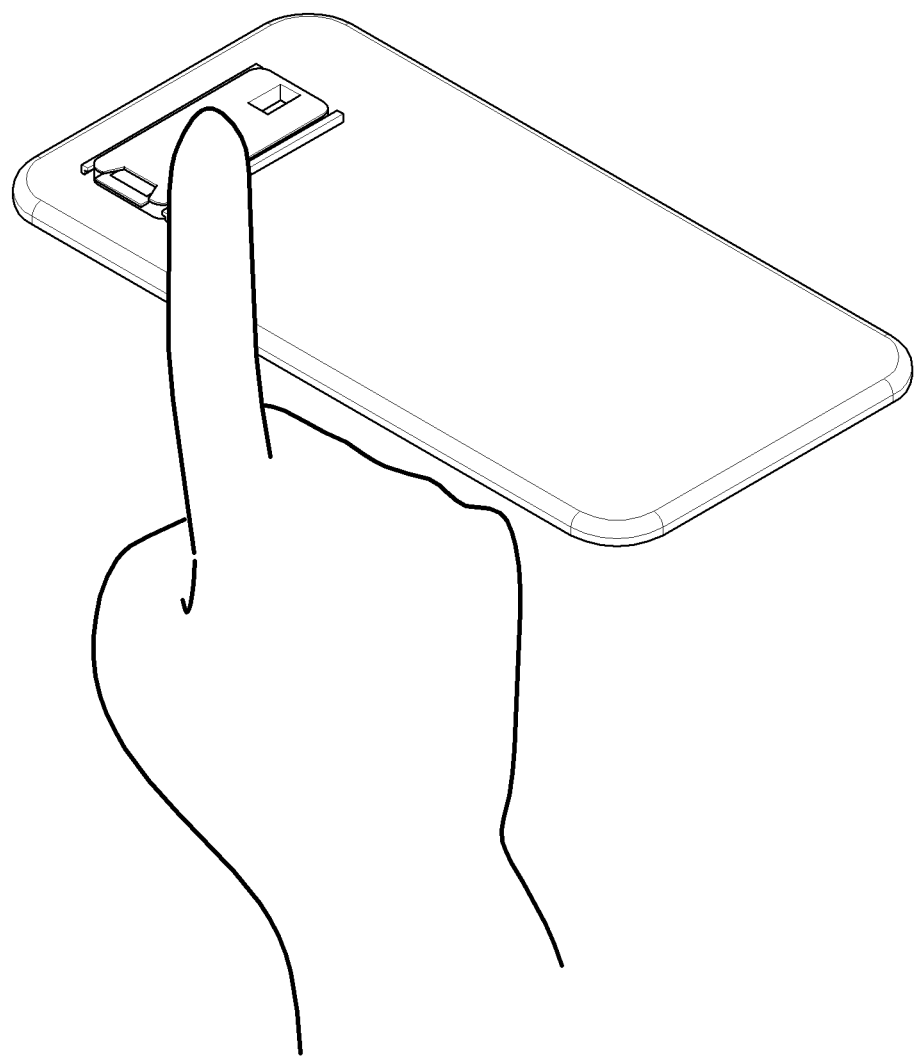
Figure 10G:
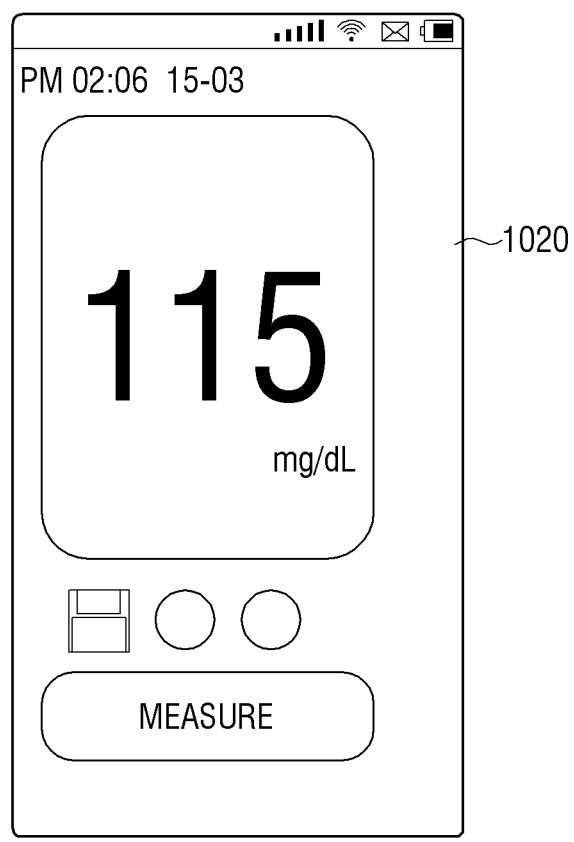

As illustrated in FIG. 10A, while an execution icon 1010 corresponding to a blood glucose level measuring application is displayed, if a command to touch the execution icon 1010 is input, the processor 370 displays the execution screen 1020 of an application for measuring blood glucose, as illustrated in FIG. 10B. On the execution screen 1020, an icon 1030 for starting measurement of a blood glucose level may be included. When the icon 1030 for starting measurement of blood glucose level is selected, the processor 370 may obtain an image by activating a camera. As illustrated in FIG. 10C, the portable terminal 300 may be turned upside down by a user such that a front surface where the display 330 is present is in a downward direction, and a rear side where the light source 310 and the camera 320 are present is in an upward direction. As illustrated in FIG. 10D, at a position of the light source 310 and the camera 320, the housing 600 including the strip module 200 is coupled. In addition, a user, as illustrated in FIG. 10E, may take blood sample, and as illustrated in FIG. 10F, may inject the taken blood sample to a hole 610 formed on the housing 600. The blood sample may be injected on the dye pad 210 provided on the transparent strip 220. The processor 370 may analyze a photographed image (red mode value) of the dye pad 210 to which blood sample is injected and measure the blood glucose level. The processor 370, as illustrated in FIG. 10G, may control the display 330 to provide the measured blood glucose level to the execution screen 1020 of the blood glucose measuring application.

Figure 11:
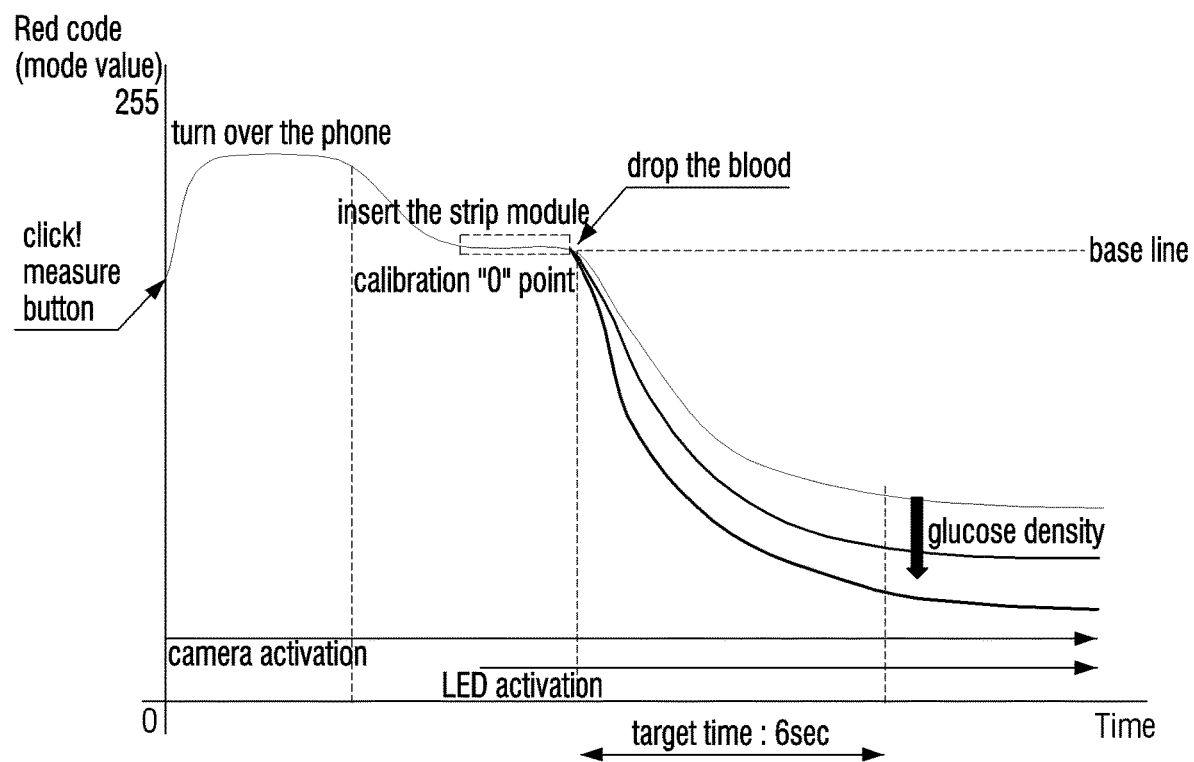
FIG. 11 is a chart illustrating a method for measuring a blood glucose level as a red mode value is changed from an image which photographs a dye pad, according to an embodiment of the present disclosure.

FIG. 11 is a chart illustrating a method for changing a red mode value in an image photographing a dye pad and measuring blood glucose levels.

As illustrated in FIG. 11, when the icon 1030 for starting measurement of the blood glucose level is selected, the camera 320 may be activated, and the portable terminal 300 may be turned over. After certain time passes, the basic mode is corrected, and the strip module 200 is inserted, the light source 310 is activated. At this time, the red mode value drastically decreases, and after certain time (for example, 6 seconds), red mode value is converged to a specific value. When the red mode value is converged to a specific value, the processor 370 determines the blood glucose value corresponding to a specific value.

Figure 12:
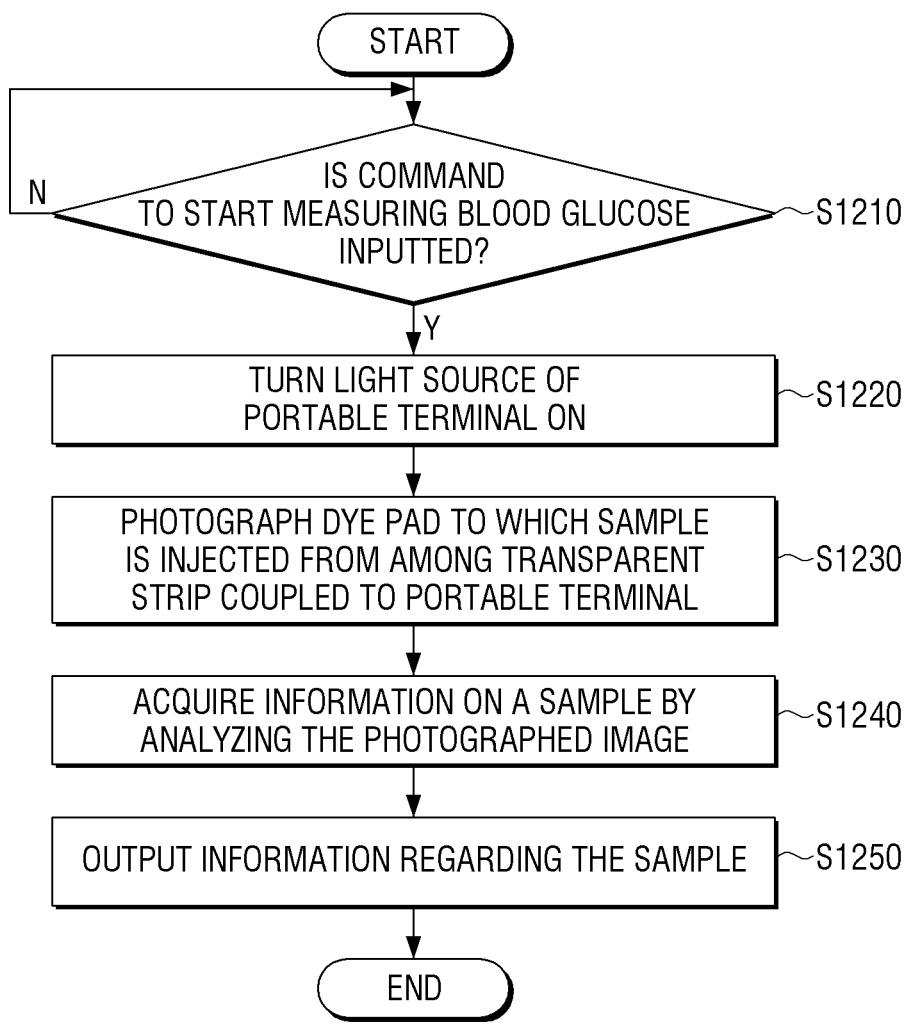
FIG. 12 is a flowchart illustrating a method for measuring a blood glucose level in a portable terminal, according to an embodiment of the present disclosure.

FIG. 12 is a flowchart illustrating a method for measuring blood glucose of a portable terminal, according to an embodiment of the present disclosure.

The portable terminal 300 determines whether a command to start measuring a blood glucose level is input, in step S1210. The command to start measuring the blood glucose level may be a user command to select the icon 1030 provided on the display 330. However, the command to start measuring blood glucose may be embodied as another type of user command (for example, voice input, gesture input, etc.).

When a command to start measuring blood glucose is input, the portable terminal 300 turns on the light source 310 of the portable terminal, in step S1220. When the strip module 200 for measuring blood glucose is coupled with the portable terminal 300, the portable terminal may turn on the light source 310.

The portable terminal 300 photographs the dye pad 210 to which a sample is injected from the transparent strip 220 coupled to the portable terminal 300, in step S1230.

The portable terminal 300 acquires information on a sample by analyzing the photographed image, in step S1240.

For example, when a sample is a blood sample, the portable terminal 300 may analyze red mode value from the photographed image and measure blood glucose of the blood sample.

The portable terminal 300 outputs information regarding the sample, in step S1250. For example, the portable terminal 300 may output information regarding the measured blood glucose level.

A user may use a portable terminal such as a smartphone without necessity to use a separate blood glucose device, and acquire information on a sample more conveniently. In addition, a manufacturing cost of a strip module is cheaper, and blood glucose levels can be measured more economically. In addition, through the strip module 200 and the portable terminal 300, various information such as fire, smoking, poison gas, smoke due to cooking, sick house syndrome, pollution of food, disease, working environment, change of environment (e.g., antibacteria, deodorization, sterilization, etc.) within home, office, working place, retail, hotel, and vehicle. At this time, the strip module 200 can be attached to internal or external tile, ceiling, glass, wallpaper, mirror, hood, and cooktop, etc. In addition, through the strip module 200 and the portable terminal 300, various information such as air cleaning level, germs, disease germs, virus, water quality, materials causing allergies within hospitals, schools, and travel spots can be acquired.

In the aforementioned example, it is described that blood glucose of a blood sample is measured by analyzing blood sample injected to a dye pad, but this is merely exemplary, and the technical spirit can be applied to inspect information of another liquid.

For example, the portable terminal 300 may photograph the dye pad 210 into which water is injected and inspect PH of water, hardness (value which converts calcium and magnesium to ppm of calcium carbonate), germs, virus, specific inorganic substance, organic substance, mineral amount, etc. Therefore, the portable terminal 300, based on water quality information, may check water quality before drinking water, check adequate water quality (for example, PH), or check water quality of a fish tank.

As still another example, the portable terminal 300 may photograph the dye pad 210 into which various food is injected to check various information of a degree of contamination, freshness, and fermentation of the food. Therefore, the portable terminal 300 may control an external device (for example, a refrigerator, air-conditioner, window, humidifier, etc.) based on various information of food.

A device (or a method may be performed by at least one computer (e.g., processor) that executes instructions included in at least one program from among the programs which are maintained in computer-readable storage media.

When the command is executed by computer (e.g. processor), the at least one computer may perform a function to correspond to the command. At this time, a storage medium readable by computer may be, for example, the memory 350.

A program may be included in computer readable storage medium, for example, hard disk, floppy disk, magnetic media (e.g., magnetic tape), optical media (e.g., compact disc read only memory (CD-ROM), digital versatile disc (DVD), magneto-optical media (ex: floptical disk), hardware device (ex: read only memory (ROM), random access memory (RAM), or flash memory, etc.). In this case, the storage medium is included as a part of the configuration of the electronic apparatus 200, but may be amounted through a port of the electronic apparatus 200, or included in an external device (for example, cloud, server, or other electronic device) located outside the electronic apparatus 200.

In addition, a program can be stored by being split into a plurality of storage medium, and in this case, at least one of a plurality of storage medium may be located at an external device of the portable terminal 300.

A command may include not only machine code made by compiler but also include high level language code which may be executed by computer using interpreter, etc. The aforementioned hardware device may be configured to be operated as one or more software module to perform various operations, and the reverse is the same.

While the present disclosure has been shown and described with reference to certain embodiments thereof, it will be understood by those skilled in the art that various changes in form and detail may be made therein without departing from the spirit and scope of the disclosure as defined by the appended claims.

What is claimed is:

1. A strip module attachable to a portable terminal including a light source, the strip module comprising:
    a dye pad having a color that changes in response to a sample applied to the dye pad; and
    a transparent strip including a first side and a second side, the first side being opposite the second side, the dye pad being mounted on the first side of the transparent strip,
    a housing that houses the transparent strip with the dye pad fixed thereto, and
    a Fresnel lens which is disposed between the dye pad and a camera of the portable terminal for reducing a focusing distance of the camera,
    wherein, based on the strip module being attached to the portable terminal, the second side of the transparent strip directly faces and completely covers the light source of the portable terminal and the transparent strip transmits light to the dye pad by reflecting light provided from the light source of the portable terminal,
    wherein the second side of the transparent strip comprises a first aperture and a second aperture,
    wherein the first aperture is positioned in an area corresponding to the camera and the second aperture is positioned in an area corresponding to the light source,
    wherein the camera of the portable terminal is operable to photograph the dye pad through the first aperture in a state in which the housing is positioned outside of the portable terminal,
    wherein the strip module further comprises a reflective coupling portion that extends perpendicular to the light source between the portable terminal and the transparent strip, and reflects the light provided from the light source towards the transparent strip,
    wherein the dye pad is implemented as a transparent polymer having a refractive index that is greater than 1,
    wherein an image of the dye pad is captured by the camera of the portable terminal located adjacent to the second side of the transparent strip,
    wherein, based on the strip module being attached to the portable terminal, a first area of the transparent strip is positioned on the light source of the portable terminal, and the transparent strip reflects the light emitted by the light source through total reflection or diffused reflection and transmits the light to a second area of the transparent strip where the dye pad is mounted, and
    wherein, when the sample is a blood sample, the dye pad comprises a blood cell removing pad to remove blood cells of the blood sample.

2. The strip module as claimed in claim 1, wherein, based on the strip module being attached to the portable terminal by a coupling unit, the dye pad is positioned on the camera of the portable terminal.

3. The strip module as claimed in claim 1, wherein the light provided from the light source of the portable terminal is white light.

4. The strip module as claimed in claim 1, wherein the dye pad is printed with a colorimetric sample.

5. The strip module as claimed in claim 1, wherein the strip module is detachable from the portable terminal or a cover case of the portable terminal, and is operable to be inserted into a guide module that guides the strip module to a position corresponding to the light source and the camera of the portable terminal.

6. The strip module as claimed in claim 1, wherein the housing comprises:
    a coupling unit operable to detach the housing from the portable terminal or a cover case of the portable terminal.

7. The strip module as claimed in claim 6, wherein the coupling unit comprises a sliding guide that moves along a rail provided on the portable terminal or the cover case of the portable terminal.

8. The strip module as claimed in claim 1, wherein the light source of the portable terminal comprises a light emitting diode (LED).

* * * * *